United States Patent [19]

Déziel et al.

[11] Patent Number: 5,380,727
[45] Date of Patent: Jan. 10, 1995

[54] SYNERGISTIC COMBINATION FOR TREATING HERPES INFECTIONS

[75] Inventors: Robert Déziel, Ville Mont-Royal; Yvan Guindon, Montreal, both of Canada

[73] Assignee: Bio-Mega, Inc., Laval, Canada

[21] Appl. No.: 809,611

[22] Filed: Dec. 17, 1991

[30] Foreign Application Priority Data

Dec. 31, 1990 [CA] Canada .................................. 2033447

[51] Int. Cl.⁶ .............................................. A61K 37/00
[52] U.S. Cl. ........................................ 514/261; 514/18
[58] Field of Search ................................... 514/18, 261

[56] References Cited

U.S. PATENT DOCUMENTS 4,294,831 10/1981 Schaeffer ............................ 424/253
4,323,573 4/1982 Schaeffer ............................ 424/253

OTHER PUBLICATIONS

Ashton et al. 116 CA:59995u 1989 (US Appl.).
Gaudreau et al. 108 CA:33969z 1988.
Freidinger et al. 110 CA:213368c 1989.

Primary Examiner—Marianne M. Cintins
Assistant Examiner—Russell Travers
Attorney, Agent, or Firm—D. E. Frankhouser; A. R. Stempel; M-E. M. Timbers

[57] ABSTRACT

Disclosed herein is a combination of an antiviral nucleoside analog and a ribonucleotide reductase inhibiting peptide derivative. The combination is useful for treating herpes infections.

16 Claims, 1 Drawing Sheet

SYNERGISTIC COMBINATION FOR TREATING HERPES INFECTIONS

FIELD OF THE INVENTION

This invention relates to an antiviral pharmaceutical composition comprising a combination of a nucleoside analog and a peptide derivative, and to a method of treating herpes infections in a mammal by administering the combination to the mammal.

BACKGROUND OF THE INVENTION

Herpes viruses inflict a wide range of diseases against humans and animals. For instance; herpes simplex viruses, types 1 and 2 (HSV-1 and HSV-2), are responsible for cold sores and genital lesions, respectively; varicella zoster virus (VZV) causes chicken pox and shingles; and the Epstein-Barr virus (EBV) causes infectious mononucleosis.

Over the past two decades, a class of compounds known as the purine and pyrimidine nucleoside analogs has been the subject of much attention by investigators in the search for new therapeutic agents for the treatment of herpes virus infections. As a result, several nucleoside analogs have been developed as antiviral agents. The most successful to date is acyclovir which is the agent of choice for treating genital herpes simplex infections. Other nucleoside analogs which are used therapeutically for the treatment of herpes infections include vidarabrine, idoxuridine, trifluridine and ganciclovir.

The mode of action by which the nucleoside analogs exert their antiviral effect is thought to involve the inhibition of viral nucleic acid replication. In the case of herpes viruses, the production of new viral deoxyribonucleic acid (DNA), an essential stage of viral replication, depends on the interaction of the virally encoded enzyme, DNA polymerase, with cellular deoxynucleotides. The nucleoside analog, when converted enzymatically in vivo to its triphosphate derivative, acts as an alternate substrate (i.e. a "fraudulent substrate") for the viral DNA polymerase, and becomes incorporated into the growing viral DNA chain. Since the nucleoside analog either lacks and essential group, e.g. the 3'-hydroxyl, or has the wrong stereochemistry, it also acts as a "chain terminator" of the growing viral DNA chain. The net effect is that the nucleoside analog acts in vivo as an inhibitor of the viral DNA polymerase.

Although the therapeutically useful nucleoside analogs have proven to be a valuable agents for combatting or controlling herpes infections, the agents are not without side effects. For example, skin rashes and renal impairment have been reported as side effects for acyclovir (see Physicians' Desk Reference, 44th ed., Medical Economics Inc., Oradell, N.J., USA, 1990, pp 819-821). For a recent review of the available antiviral drugs and their side effects, see M. C. Nahata, "Antiviral Drugs: Pharmacokinetics, Adverse Effects, and Therapeutic Use", J. Pharm. Technol., 3, 100 (1987). Hence, safety as well as cost advantages would be realized if these agents were formulated in a manner which enhanced their therapeutic activity.

We now have found that the antiviral activity of the nucleoside analogs can be enhanced synergistically, without concomitant enhancement of toxic effects, by combining the same with certain peptide derivatives having selective herpes ribonucleotide reductase inhibiting properties.

Ribonucleotide reductase (RR) is the enzyme responsible for the conversion of ribonucleotides to deoxyribonucleotides. The role of RR in DNA biosynthesis has been reviewed recently by J. Stubbe, J. Biol. Chem. 265, 5329 (1990).

In 1985, T. Spector et al., Proc. Natl. Acad. Sci. USA, 82, 4254 (1985) reported that a combination of acyclovir and a semicarbazone RR inhibitor, 2-acetylpyridine thiosemicarbazone, produced a synergistic antiherpes effect. However, the combination of acyclovir with the RR inhibitor hydroxyurea was toxic to the host cell and acyclovir combined with some related semicarbazone derivatives did not always potentiate the antiherpes activity of acyclovir.

A three-way combination of acyclovir, bacitracin and an RR inhibiting nonapeptide has been reported by E. A. Cohen et al., U.S. Pat. No. 4,795,740, Jan. 3, 1989. Curiously, the antiherpes activity of the latter combination was indicated as being equal or less than acyclovir alone.

Still other synergistic combinations containing a nucleoside analog as a component have been reported; for example:

T. P. Zimmerman and G. Wolberg, European patent application 235931, published Sep. 9, 1987 (nucleoside analogs plus nucleoside transport inhibitors);

K. O. Smith, Canadian patent 1,239,093, issued Jul. 12, 1988 (nucleoside analog plus an interferon);

T. Spector et al., Proc. Natl. Acad. Sci. USA, 86, 1051 (1989), (nucleoside analog plus RR inhibitor);

T. Spector et al., U.S. Pat. No. 4,758,572, issued Jul. 19, 1988 (nucleoside analogs plus RR inhibitors); and T. A. Blumenkopf et al, European patent application 349,243, published Jan. 3, 1990 (nucleoside analogs plus RR inhibitors).

The combination of the present invention can be distinguished from the preceding combinations by its different composition and/or its relative lack of toxicity.

SUMMARY OF THE INVENTION

Provided herein is a pharmaceutical composition for treating herpes infections in a mammal comprising a pharmaceutically or veterinarily acceptable carrier, and an effective amount of the combination of an antiviral nucleoside analog, or a therapeutically acceptable salt thereof, and a ribonucleotide reductase inhibiting peptide derivative of formula 1

$$R^1NHC(O)CH_2CHR^4C(O)-NR^3-CH[CH_2-C(O)-Y]C(O)-NH-CH[CR^4(R^5)COOH]-C(O)-NH-CHR^6-Z \qquad 1$$

wherein $R^1$ is (1-10C)alkyl, (1-10C)alkyl monosubstituted with halo, hydroxy or lower alkoxy, lower cycloalkyl, (lower cycloalkyl)-(lower alkyl), phenyl(lower)alkyl or phenyl(lower)alkyl monosubstituted with halo, hydroxy or lower alkoxy;

$R^2$ is lower alkyl;

$R^3$ is hydrogen or lower alkyl;

$R^4$ is hydrogen or lower alkyl and $R^5$ is lower alkyl, or $R^4$ and $R^5$ together with the carbon atom to which they are attached form a lower cycloalkyl;

$R^6$ is lower alkyl, lower cycloalkyl or (lower cycloalkyl)-(lower alkyl);

Y is (a) $NR^7R^8$ wherein $R^7$ and $R^8$ each independently is lower alkyl, or $R^7$ and $R^8$ together with the nitrogen atom to which they are attached form a pyrrolidino, piperidino, morpholino, thiomorpholino, piperazino or $N^4$-methylpiperazino; or (b) (1–7C)alkyl, lower cycloalkyl or (lower cycloalkyl)methyl; and Z is hydrogen, COOH or $CH_2OH$;

or a therapeutically acceptable salt thereof.

The antiviral nucleoside analog employed in the combination is one which is enzymatically convertible (in vivo) to a viral DNA polymerase inhibitor of, and/or an alternative substrate for, a herpes DNA polymerase. The antiviral nucleoside analog can be selected from known nucleoside analogs. Preferred nucleoside analogs of the invention include acyclovir and its analogs; for example, the compounds of formula 2

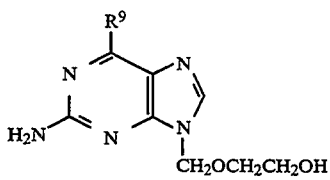

wherein $R^9$ is hydrogen, hydroxy or amino, or a therapeutically acceptable salt thereof. (Formula 2 wherein $R^9$ is hydroxy represents acyclovir.)

Other preferred antiviral nucleoside analogs for use according to the present invention include vidarabine, idoxuridine, trifluridine, ganciclovir, edoxudine, brovavir, fiacitabine, penciclovir, famciclovir and rociclovir.

A preferred group of the peptide derivatives for use according to the present invention is represented by formula 1 wherein $R^1$ is (1–10C)alkyl, (1–10C)alkyl monosubstituted with halo, hydroxy or lower alkoxy, lower cycloalkyl or (lower cycloalkyl)methyl, $R^2$ is lower alkyl, $R^3$ is hydrogen, $R^4$ and $R^5$ together with the hydrogen to which they are attached form a lower cycloalkyl, and $R^6$, Y and Z are as defined hereinabove; or a therapeutically acceptable salt thereof.

A more preferred group of the peptides derivatives is represented by formula 1 wherein $R^1$ is 1-methylethyl, 1-methylpropyl, 1-ethylpropyl, 1-methylbutyl, cyclopentyl or cyclohexyl, $R^2$ is methyl, ethyl, propyl, 1-methylethyl, butyl, 1-methylpropyl, 2-methylpropyl, 1,1-dimethylethyl or 1-methylbutyl, $R^3$, $R^4$ and $R^5$ are as defined hereinabove, $R^6$ is 1-methylethyl, 1,1-dimethylethyl, 1-methylpropyl, 2-methylpropyl, 2,2-dimethylpropyl, cyclopentyl, cyclohexyl or cyclohexylmethyl, Y is $NR^7R^8$ wherein $R^7$ and $R^8$ each independently is methyl, ethyl or propyl or $R^7$ and $R^8$ together with the nitrogen atom to which they are attached form a pyrrolidino, piperidino, morpholino or $N^4$-methylpiperazino, or Y is pentyl, hexyl, 4-methylpentyl, heptyl, cyclopentyl or cyclohexyl, and Z is as defined hereinabove; or a therapeutically acceptable salt thereof.

A most preferred group of the peptide derivatives is represented by formula 1 wherein $R^1$ is 1-methylethyl or 1-ethylpropyl, $R^2$ is 1-methylethyl or 1,1-dimethylethyl, $R^3$ is hydrogen, $R^4$ and $R^5$ together with the carbon atom to which they are attached form a cyclobutyl or cyclopentyl, $R^6$ is 2,2-dimethylpropyl, Y is N,N-dimethylamino, N,N-diethylamino, pyrrolidino, morpholino or $N^4$-methylpiperazino, hexyl, heptyl or cyclopentyl, and Z is as defined hereinabove; or a therapeutically acceptable salt thereof.

Included within the scope of the invention is a cosmetic composition comprising a herpes viral prophylactic amount of the combination of an antiviral nucleoside analog of formula 2 wherein $R^9$ is a defined herein above, or a therapeutically acceptable salt thereof; a ribonucleotide reductase inhibiting peptide derivative of formula 1, or a therapeutically acceptable salt thereof; and a physiologically acceptable carrier.

Also included is a method of treating herpes viral infections in a mammal which comprises administering thereto an effective amount of a combination of an antiviral nucleoside analog and the ribonucleotide reductase inhibiting peptide derivative of formula 1, or a therapeutically acceptable salt thereof.

DETAILS OF THE INVENTION

Figure 1:
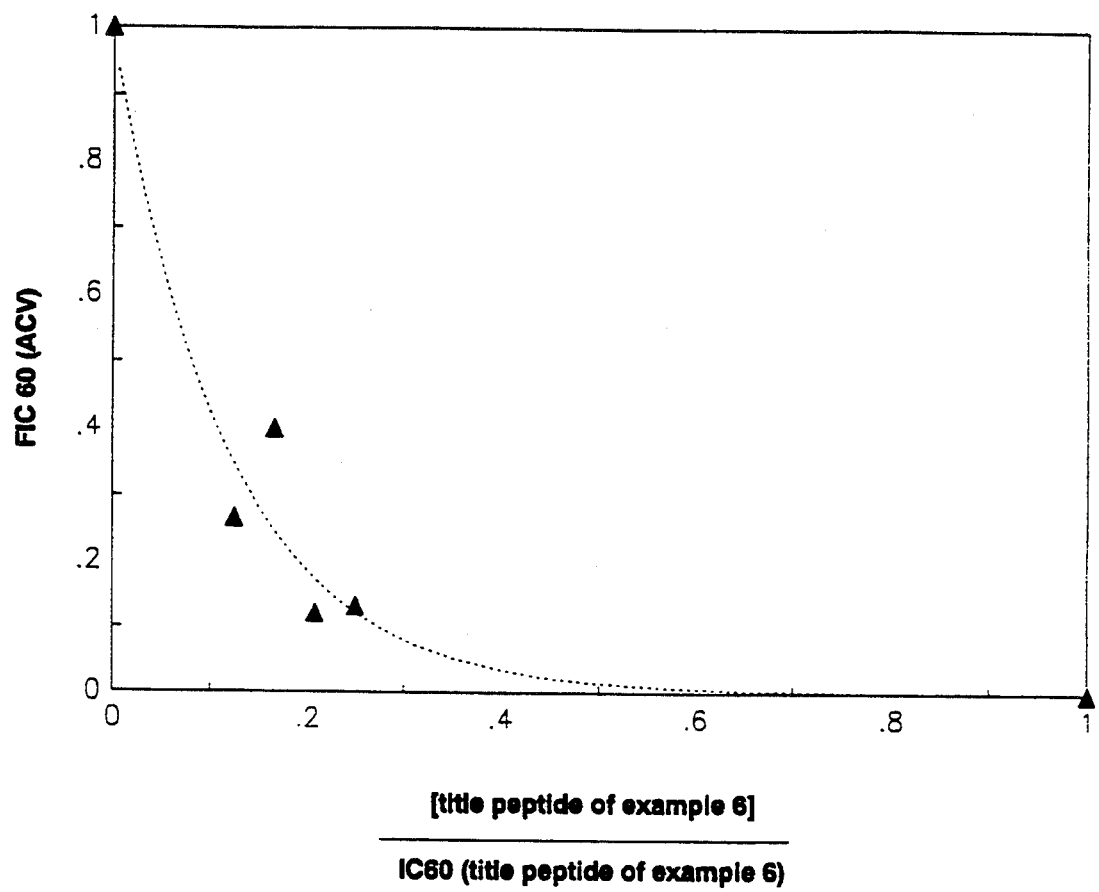
FIG. 1 is an isobologram showing the synergistic inhibition of HSV-2 replication by the peptide of formula 1, $Et_2CHNH-COCH_2CH[(S)-C(CH_3)_3]CO$-Asp(pyrrolidino)-Asp(cyPn)-YMeLeu-OH and acyclovir (see example 6). The concentration of the peptide was varied and the inhibition of virus replication was assessed. The FIC60 (acyclovir) is the ratio of the concentration of acyclovir required tip inhibit virus replication by 60% in the presence of a given concentration of the peptide. The x axis is the ratio of a given concentration of the peptide to the concentration the peptide producing 60% inhibition of virus replication in the absence of acyclovir.

The antiviral nucleoside analogs, and their therapeutically acceptable salts, for use according to the present invention are a well known class of compounds. As noted above, the members of this class are characterized by the manner in which they mediate an antiviral effect against herpes viruses, i.e. by in vivo inhibition of viral DNA polymerase. Important members of this class are acyclovir and its analogs which are described by H. J. Schaeffer in U.S. Pat. No. 4,199,574, issued Apr. 22, 1980; see also H. J. Schaeffer et al., Nature (London), 272, 583 (1978) and T. A. Krenitsk et al., Proc. Natl. Acad. Sci. USA, 81, 3209 (1984). The compound of formula 2 wherein $R^9$ is hydroxy is "acyclovir", also known by its chemical name, 9-[(2-hydroxyethoxy)methyl]guanine. The compound of formula 2 wherein $R^9$ is hydrogen has the names 6-deoxyacyclovir and 2-amino-9-[(2-hydroxyethoxy)methyl]adenine; and the compound of formula 2 wherein $R^9$ is amino has the chemical name, 2,6-diamino-9-[(2-hydroxyethoxy)methyl]purine.

Is to be understood that the compound of formula 2 in which $R^9$ is hydroxy can exist in its tautomeric form, i.e. 2-amino-1,9-dihydro-9-[(2-hydroxyethoxy)methyl]-6H-purin-6-one, and that the compound can be a mixture of the two tautomeric forms, the percentage of each tautomer in the mixture being dependent on the physical environment of the compound. Tautomeric forms also are possible for the other antiviral nucleoside analogs having an enolizable carbonyl.

Other antiviral nucleotides contemplated for use according to the present invention include vidarabine (9-$\beta$-D-arabinofuranosyladenine monohydrate), see R. J. Whitley et al., N. Engl. J. Med., 307, 971 (1982); idoxudine (2'-deoxy-5-iodouridine), see W. H. Prusoff, Biochim. Biophys. Acta, 32, 295 (1959); trifluridine [2'-deoxy-5-(trifluoro-methyl)-uridine], see C. Heidelberger, U.S. Pat. No. 3,201,387, issued Aug. 17, 1965;

ganciclovir 9-[(1,3-dihydroxy-2-propoxy)methyl]guanine, see J. P. Verheyden and J. C. Martin, U.S. Pat. No. 4,355,032, issued Oct. 19, 1982; edoxudine (5-ethyl-2'-deoxyuridine), see K. K. Gauri, U.S. Pat. No. 3,553,192, issued Jan. 5, 1971; brovavir [(E)-5-(2-bromovinyl)-2'-deoxyuridine], see Y. Benoît et al., Eur. J. Pediatrics, 143, 198 (1985); fiacitabine (2'-fluoro-deoxy-5-iodouridine), see B. Leyland-Jones et al., J. Infect. Dis., 154, 430 (1986), penciclovir (9-[4-hydroxy-3-(hydroxymethyl)butyl]guanine, see S. E. Fowler et al., Br. J. Clin. Pharmacol., 28, 236P (1989); famciclovir (9-[4-acetoxy-3-(acetoxy-methyl)butyl]adenine, see R. A. V. Hodge et al., Antimicrob. Agents Chemotherap., 33, 1765 (1989); and rociclovir (9-[(1,3-diisopropoxy-2-propoxy)methyl]adenine, see E. Winklemann et al., Arzneim.-Forsch., 38, 1545 (1988).

For convenience, the RR inhibiting peptide derivatives of this invention are sometimes designated hereinafter as the peptides of formula 1.

With reference to the peptides of formula 1, the abbreviations used herein for designating the amino acids and the protective groups are based on recommendations of the IUPAC-IUB Commission of Biochemical Nomenclature, see European Journal of Biochemistry, 138, 9 (1984). For instance, Val, Ala, Ile, Asp and Leu, represent the residues of L-valine, L-alanine, L-isoleucine, L-aspartic acid and L-leucine, respectively.

The asymmetric carbon atoms residing in the principal linear axis (i.e. the backbone) of the peptides of formula 1, exclusive of the 1,4-dioxobutyl moiety and the terminal groups, have an S configuration. Asymmetric carbon atoms residing in the side chain of an amino acid or derived amino acid residue, in the 1,4-dioxobutyl moiety or in a terminal group, may have the S or R configuration.

The term "residue" with reference to an amino acid or amino acid derivative means a radical derived from the corresponding α-amino acid by eliminating the hydroxyl of the carboxy group and one hydrogen of the α-amino group.

The term "halo" as used herein means a halo radical selected from bromo, chloro, fluoro or iodo.

The term "lower alkyl" as used herein, either alone or in combination with a radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl. The term "(1–7C)alkyl" as used herein means straight chain alkyl radicals containing one to seven carbon atoms and branched chain alkyl radicals containing three to seven carbon atoms. The term "(1–10C)alkyl" similarly contemplates those alkyl radicals containing from one to ten carbon atoms.

The term "lower cycloalkyl" as used herein, either alone or in combination with a radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tertiary-butyloxy.

The symbol "Tbg" represents the amino acid residue of 2(S)-amino-3,3-dimethylbutanoic acid. The symbol "Cpg" represents the amino acid residue of (S)-α-aminocyclopentaneacetic acid. The symbol "Cha" represents the amino acid residue of (S)-α-aminocyclohexanepropionic acid. The term "YMe-Leu" represents the amino acid residue of 2(S)-amino-4,4-dimethylpentanoic acid.

Other symbols used herein are: (N-Me)Asp for the residue of (S)-2-(methylamino)butanedioic acid; Asp(cyBu) for the residue of (S)-α-amino-1-carboxycyclobutaneacetic acid; Asp(cyPn) for the residue (S)-α-amino-1-carboxycyclopentaneacetic acid; Asp(pyrrolidino) for the residue of the amide 2(S)-α-amino-4-oxo-4-pyrrolidinobutanoic acid; and Asp(morpholino) and Asp(NEt$_2$) similarly represent the residues of the corresponding amides wherein the pyrrolidino is replaced with morpholino and diethylamino respectively. The symbol "Asp(diMe)" represents the residue of 2(S)-amino-3,3-dimethylbutanedioic acid, i.e. 3,3-dimethyl-L-aspartic acid.

The ribonucleotide reductase (RR) inhibiting peptides of formula 1, and their therapeutically acceptable salts, are prepared by processes described by P. L. Beaulieu, R. Déziel and N. Moss in U.S. patent application Ser. No. 711,232, filed Jun. 6, 1991. More specifically, the peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schröder and K. Lübke, "The Peptides", Vol. 1, Academic Press, New York, N.Y., 1965, pp 2–128, in the textbook series, "The Peptides: Analysis, Synthesis, Biology", E. Gross et al., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptides is the protection of the reactive side chain groups of the various amino acid residues or derived amino acid residues with suitable protective groups which will prevent a chemical reaction from occurring at that site until the protective group is ultimately removed. Usually also common is the protection of an α-amino group on an amino acid or a fragment while that entity reacts at the carboxy group, followed by the selective removal of the α-amino protective group to allow subsequent reaction to take place at that location. Usually another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

In general, therefore, a peptide of formula 1 can be prepared by the stepwise coupling in the order of the sequence of the peptide of the amino acid or derived amino acid residues, or fragments of the peptide, which if required are suitably protected, and eliminating all protecting groups, if present, at the completion of the stepwise coupling to obtain the peptide of formula 1.

The term "pharmaceutically acceptable carrier" as used herein means a non-toxic, generally inert vehicle for the active ingredients, which does not adversely affect the active ingredients.

The term "physiologically acceptable carrier" as used herein means an acceptable cosmetic vehicle of one or more non-toxic excipients which do not react with or reduce the effectiveness of the active ingredients contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "synergistic effect" when used in relation to the antiviral or antiherpes activity of the above defined combination of the nucleoside analog and peptide of formula 1 means an antiviral or antiherpes effect which is greater than the predictive additive effect of the two individual components of the combination.

The antiviral activity of the combination of this invention can be demonstrated by biochemical, microbiological and biological procedures showing the inhibitory effect of the combination on the replication of HSV-1 and HSV-2, and other herpes viruses, for example, varicella zoster virus (VZV), Epstein-Barr virus (EBV), equine herpes virus (EHV) and pseudorabies virus (PRV).

For example, a method for demonstrating the inhibitory effect of the combination on viral replication is the cell culture technique; see, for example, T. Spector et al., Proc. Natl. Acad. Sci. USA, 82, 4254 (1985). This method in a modified form is exemplified hereinafter.

A method for demonstrating the therapeutic effect of the combination is the guinea pig model for cutaneous herpes simplex viral infections; see, for example, S. Alenius and B. Oberg, Archives of Virology, 58, 277 (1978).

When utilizing the combination of this invention for treating viral infections, the combination is administered to warm blooded animals, e.g. humans, pigs or horses, in a vehicle comprising one or more pharmaceutically acceptable carriers, the proportion of which is determined by the solubility and chemical nature of the nucleoside analog and the peptide of formula 1, chosen route of administration, standard biological practice, and by the relative amounts of the two active ingredients to provide a synergistic antiviral effect. Preferably, the combination is administered topically. For example, the two active agents (i.e. the antiviral nucleoside analog and the peptide of formula 1, or their therapeutically acceptable salts) can be formulated in the form of solutions, emulsions, creams, or lotions in pharmaceutically acceptable vehicles. Such formulation can contain 0.01–1.0%, preferably 0.05–0.5%, by weight of the nucleoside analog, or a therapeutically acceptable salt thereof, and about 0.5–20%, preferably 1–10%, by weight of the peptide of formula 1, or a therapeutically acceptable salt thereof.

In any event, the two active agents are present in the pharmaceutical composition in amounts to provide a synergistic antiherpes effect.

One preferred embodiment of this invention involves an antiviral pharmaceutical composition for treating herpes viral infections of the skin or part of the oral or genital cavity. This composition comprises a combination of 0.05–1.0% by weight of the nucleoside analog of formula 2 in which $R^9$ is hydroxy, 1–10% by weight of the peptide of formula 1 wherein $R^2$ is 1,1-dimethylethyl (with an orientation that imparts an (S) configuration to the 1,4-dioxo moiety), $R^4$ and $R^5$ together with the carbon atom to which they are attached form a cyclobutyl or cyclopentyl and $R^6$ is 2,2-dimethylpropyl, together with a pharmaceutically acceptable carrier. Preferred carriers in this instance are water soluble ointment bases or water-oil type emulsions.

Examples of suitable excipients or carriers for the above mentioned formulations are found in standard pharmaceutical texts, e.g. in "Remington's Pharmaceutical Sciences", 18th ed, Mack Publishing Company, Easton, Pa., 1990.

The dosage of the combination of this invention will vary with the form of administration and the particular active agents chosen for the combination. Furthermore, it will vary with the particular host under treatment. Generally, treatment is initiated with small dosages substantially less than the optimum dose of the combination. Thereafter, the dosage is increased by small increments until the optimum effect under the circumstances is reached. In general, the combination is most desirably administered at a concentration level that will generally afford antiviral effective results against herpes virus without causing any harmful or deleterious side effects.

The combinations is administered topically to the infected area of the body, e.g. the skin or part of the oral or genital cavity, in an amount sufficient to cover the infected area. The treatment should be repeated, for example, every four to six hours until lesions heal.

Although the method of treating herpes viral infections can be most advantageously practised by administering the combination of the nucleoside analog and the peptide of formula 1 simultaneously in a formulation, the separate or sequential administration on a daily basis of the two active agents is also encompassed within the scope of this invention.

Another embodiment of this invention comprises a cosmetic composition comprising a herpes viral prophylactic amount of the combination of this invention, together with a physiologically acceptable cosmetic carrier. Additional components, for example, skin softeners, may be included in the formulations. The cosmetic formulation of this invention is used prophylactically to prevent the outbreak of herpetic lesions. They can be applied nightly and generally contain less of the two active agents of the combination than pharmaceutical preparations. A preferred range for the amount of each of the agents in the cosmetic composition is 0.01–0.1% by weight of the nucleoside analog and 0.1 to 1% by weight of the peptide of formula 1.

The following examples illustrate further this invention. Solution percentages or ratios express volume to volume relationship, unless stated otherwise. Abbreviations used in the examples include; Boc: t-butyloxy-carbonyl; BOP: (benzotriazol-1-yloxy)tris(dimethylamino)-phosphonium hexafluorophosphate; Bzl: benzyl; $CH_2Cl_2$: methylenedichloride; DIPEA: diisopropylethylamine; DCC: N,N-dicyclohexylcarbodiimide; DMF: dimethyl formamide; $Et_2O$: diethyl ether; EtOAc: ethyl acetate; EtOH: ethanol; HOBt: 1-hydroxybenzotriazole; HPLC: high performance liquid chromatography; MeOH: methanol; NMM: N-methylmorpholine; TFA: trifluoroacetic acid; THF: tetrahydrofuran; TLC: thin layer chromatography. Temperatures are given in degrees centigrade.

EXAMPLE 1

Preparation of the Intermediate Boc-Asp(pyrrolidino)-OH

N,N'-Carbonyldiimidazole (24.32 g, 0.15 mol) was added in small portions to a stirred solution of Boc-Asp-OBzl (47.60 g, 0.147 mol) in acetonitrile (500 mL). After 45 min, the reaction mixture was cooled to 0° and pyrrolidine (13.4 mL, 0.16 mol) was added dropwise. Thereafter, the mixture was stirred at room temperature to complete the reaction (about 3 h as judged by TLC). The solvent was removed under reduced pressure and the residue was dissolved in EtOAc (500 mL). The organic phase was washed with 10% aqueous HCl (3×100 mL), 1N aqueous NaOH (2×100 mL) and dried ($MgSO_4$). Evaporation of the organic phase under reduced pressure gave a colorless oil which solidified on standing. The latter product in a solution of EtOH (200 mL) was subjected to hydrogenolysis for 20 h at atmospheric pressure using 200 mg of 20% by weight of Pd(OH)$_2$ on carbon as the catalyst. The reaction mixture was filtered through diatomaceous earth. Evaporation of the filtrate afforded a residue which was purified by recrystallization from hexane/Et$_2$O to give the desired product (37.10 g, 88%), mp 114°–116°. The structure of the product was confirmed by NMR.

Corresponding N-substituted asparagine analogs were obtained by replacing pyrrolidine in the procedure of this example with the appropriate amine (e.g. diethylamine or piperidine).

(b) Preparation of the Intermediate Boc-2(S)-Amino-4-oxo-undecanoic Acid

Boc-Asp-OBzl (500 mg, 1.55 mmol) was dissolved in acetonitrile (10 mL) and N,N'-carbonyldiimidazole (277 mg, 1.71 mmol) was added to the solution. After 30 min, p-nitrobenzyl-magnesium malonate (860 mg, 1.71 mmol) was added and the mixture was stirred at room temperature (20°–22°) for 1.5 h. The acetonitrile was evaporated. The residue was dissolved in EtOAc, washed with 1N aqueous HCl, water and then brine. The organic phase was dried ($MgSO_4$) and concentrated under reduced pressure. The resulting residue was purified by chromatography ($SiO_2$, eluent: hexane-EtOAc) to give Boc-2(S)-amino-4-oxo-1,6-hexanedioic acid 1-benzyl ester 6-(4-nitrophenyl)methyl ester (600 mg, 80%). The latter compound (3.25 g, 6.5 mmol) was dissolved in DMF (40 mL). Cs$_2$CO$_3$ (2.33 g, 7.14 mmol) and hexyl iodide (1.51 g, 7.14 mmol) were added to the solution. The mixture was stirred at room temperature for 18 h. The solvent was evaporated. The residue was dissolved in EtOAc. The solution was washed with 1N aqueous HCl and H$_2$O, dried ($MgSO_4$) and evaporated. The residue was purified by chromatography ($SiO_2$, eluent=hexane-EtOAc) to give Boc-2(S)-amino-4-oxo-5-[(4-nitrophenyl)methoxycarbonyl]undecanoic acid benzyl ester (630 mg). A solution of the latter compound (630 mg) in MeOH (25 mL) was shaken on a Parr apparatus under an atmosphere of H$_2$ in the presence of 20% Pd(OH)$_2$/C (70 mg) for 18 h. After filtration and concentration of the reaction mixture, the resulting residue was dissolved in EtOAc. The solution was stirred with 1N aqueous HCl for 10 min. The organic phase was separated, washed with H$_2$O, dried ($MgSO_4$) and evaporated. The residue was purified by chromatography ($SiO_2$, eluent: hexane-EtOAc) to give the title compound (160 mg). NMR and MS of the product were in agreement with the expected structure.

The coupling of the latter intermediate with appropriate units for the preparation of peptides of formula 1 in which Y is heptyl was achieved with DCC/HOBt as the coupling agent.

(c) Preparation of the Intermediate Boc-2(S)-Amino-5-cyclopentyl-4-oxocyclopentanoic Acid Boc-2(S)-amino-4-oxo-1,6-hexanedioic acid 1-benzyl ester 6-(4-nitrophenyl)methyl ester (4.8 g, 9.6 mmol) was dissolved in DMF (100 mL). Na$_2$CO$_3$ (4.07 g, 38.4 mmol) and 1,4-diiodobutane (3.59 g, 11.6 mmol) were added to the solution. The mixture was stirred 18 h at room temperature and then heated at 50° for 3 h. Evaporation of the reaction mixture, extraction of the resulting residue with EtOAc, washing of the extract with 1N aqueous HCl and water, drying (MgSO$_4$) and evaporation of the extract gave a crude product. The crude product was purified by chromatography (SiO$_2$, eluent: hexane-EtOAc) to give the corresponding benzyl ester of the title compound (4.3 g). The benzyl ester of the latter compound was subjected to hydrogenolysis [5% Pd(OH$_2$)/C in MeOH, 18 h] and worked up (see section (a) of this example) to give the title compound (140 mg). NMR and MS of the product were in agreement with the expected structure.

The coupling of the latter intermediate with other appropriate units for the preparation of peptides of formula 1 in which Y is cyclopentyl was achieved with BOP.

EXAMPLE 2

Preparation of (S)-α-Azido-1-[(phenylmethoxy)carbonyl]cyclopentaneacetic Acid Benzyl Ester The title compound was prepared from 2-oxaspiro[4.4]nonane-1,3-dione, described by M. N. Aboul-Enein et al., Pharm. Acta Helv., 55, 50 (1980), according to the asymmetric azidation method utilizing the Evan's auxiliary, see D. A. Evans et al., J. Amer. Chem. Soc., 112, 4011 (1990). The NMR (200 MHz, CDCl$_3$) of the compound showed: δ 4.55 (s,1H), 5.12 (s,2H) and 7.4 (m,5H).

EXAMPLE 3

Preparation of (R,S)-3-(1,1-dimethylethyl)-dihydro-2,5-furandione (a) A mixture of pivaldehyde (5.00 g, 58 mmol), ethylcyanoacetate (6.60 g, 58.3 mmol), acetic acid (3.50 g, 58.3 mmol) and pyridine (4.60 g, 58.2 mmol) was heated at reflux for 1 h. A second portion of pivaldehyde (5.00 g, 58 mmol) was added. The refluxing of the mixture was continued for 18 h. After cooling, the mixture was poured into 1N aqueous HCl (50 mL). The resulting mixture was extracted with EtOAc (3×50 mL). The combined organic layers were washed with 1N aqueous HCl, dried (MgSO$_4$) and concentrated to give a colorless oil. The oil was purified by flash chromatography on SiO$_2$ using hexane-EtOAc (9:1) as the eluant to give 2-cyano-4,4-dimethyl-2-pentenoic acid ethyl ester as a colorless oil (7.69 g, 73% yield).

(b) The latter compound (7.69 g, 42.4 mmol) was mixed with glacial AcOH (2.60 g, 43 mmol) and anhydrous pyridine (3.42 g, 43 mmol). The mixture was heated to 50°. Potassium cyanide was added, followed by the addition of anhydrous EtOH (6 mL). The mixture was heated at 50° for 45 min, cooled to room temperature and partitioned between 1N aqueous HCl (25 mL) and Et$_2$O (100 mL). The Et$_2$O layer was separated, washed with 1N aqueous HCl (2×20 mL) and brine (2×20 mL), dried (MgSO$_4$) and concentrated to give 2,3-dicyano-4,4-dimethylpentanoic acid ethyl ester as a brown oil (8.83 g, 100% crude yield).

(c) The latter product (11 g) was suspended in concentrated HCl (150 mL). The mixture was heated at reflux for 24 h and then cooled in an ice bath. The resulting white solid precipitate was collected, washed with water and dried under vacuum. The solid was dissolved in EtOAc (300 mL). Insoluble material in the solution was removed by filtration. The filtrate was concentrated under reduced pressure to give an oil. The oil was triturated with hexane. The resulting white crystalline material was collected to give (R,S)-2-(1,1-dimethylethyl)-1,4-butanedioic acid (7.95 g, 95% yield).

(d) The latter compound (7.95 g, 51 mmol) was suspended in acetic anhydride (11 mL, 117 mmol). The mixture was heated at 110° for 2 h. Subsequent distillation under vacuum of the mixture gave the title compound of this example as an oil (bp 140°–145°/12 mm, 7.08 g, 88% yield). The oil solidified upon cooling.

EXAMPLE 4

Preparation of
(R,S)-2-(1,1-Dimethylethyl)-4-oxo-4-(1-ethyl-propylamino)butanoic Acid (R,S)-3-(1,1-dimethylethyl)-dihydro-2,5-furandione (5.00 g, 32 mmol, described in example 3) was dissolved in acetonitrile (50 mL). The solution was cooled to 0°. (1-Ethylpropyl)amine (6.13 g), 70.4 mmol) was added slowly to the stirred solution. The solution was stirred at room temperature for 18 h and then partioned between Et$_2$O and 10% aqueous citric acid (60 mL each). The organic phase was separated. The aqueous phase was extracted with Et$_2$O (3×25 mL). The combined organic layers were washed with 10% aqueous citric acid (2×25 mL), brine (25 mL), dried (MgSO$_4$) and concentrated. The residue was triturated with Et$_2$O to give the title compound as a white solid (4.65 g, 59% yield).

EXAMPLE 5

Preparation of
Et$_2$CHNH-COCH$_2$CH[(S)-C(CH$_3$)$_3$]CO-Asp(pyr-rolidino)-Asp(cyPn)-YMeLeu-OH (a) A solution of Boc-YMeLeu-OBzl (0.272 g, 0.81 mmol) in 30% TFA in CH$_2$Cl$_2$ was stirred at 0° for 1 h. The solvent was evaporated and the residue was dried under vacuum. The resulting TFA salt was dissolved in acetonitrile (20 mL). NMM (0.53 mL, 4.86 mmol) was added to the solution, followed by the addition of (S)-α-azido-1-[(phenylmethoxy)carbonyl]cyclopentaneacetic acid (0.269 g, 0.89 mmol, described in example 2) and BOP (0.464 g, 1.05 mmol). The mixture was stirred at room temperature for 18 h. The solvent was evaporated. The residue was dissolved in EtOAc (50 mL). The solution was washed with 10% aqueous HCl (2×25 mL), a saturated aqueous solution of Na$_2$CO$_3$ (2×25 mL) and brine (25 mL). Evaporation of the organic phase gave N-{(S)-α-azido-1-[(phenylmethoxy)-carbonyl]cyclopentaneacetyl}-2(S)-amino-4,4-dimethylpentanoic acid benzyl ester as a yellow oil (0.400 g, 96% yield).

(b) A solution of the latter compound (0.312 g, 0.6 mmol) in MeOH (20 mL) was added dropwise to a solution of SnCl$_2$ (0.207 g, 1.2 mmol) in MeOH (10 mL) at 0°. The mixture was stirred under argon for 4 h while the reaction temperature was allowed to come to room temperature. The reaction mixture was concentrated under reduced pressure. The residue was dissolved in EtOAc (50 mL). The solution was rendered basic by the addition of 5% aqueous NaHCO$_3$. The organic phase was separated, washed with H$_2$O (20 mL) and brine (20 mL), dried over anhydrous K$_2$CO$_3$, filtered and concentrated to dryness to give N-{(S)-α-amino-1-[(phenylmethoxy)carbonyl]cyclopentaneacetyl}-2(S)-amino-4,4-dimethylpentanoic acid benzyl ester as a white solid (0.300 g, 0.6 mmol).

(c) The latter amine was dissolved in acetonitrile (20 mL). NMM (0.39 mL, 3.6 mmol), Boc-Asp(pyrrolidino)-OH (0.343 g, 1.2 mmol, described in example 1) and BOP (0.583 g, 1.32 mmol) were added to the solution. The mixture was stirred at room temperature for 18 h. The solvent was evaporated and the residue was dissolved in EtOAc (50 mL). The solution was washed with 10% aqueous HCl (2×20 mL), a saturated aqueous solution of Na$_2$CO$_3$ and brine. Thereafter, the solution was dried (MgSO$_4$) and concentrated to dryness. The residue was purified by flash chromatography [SiO$_2$, eluant=EtOAc-hexane, 1:1)] to give N'-[N-(tertiary-butyloxycarbonyl)-2(S)-amino-4-oxo-4-pyrrolidinobutanoyl]-N-{α-amino-1-[(phenylmethoxy)carbonyl]cyclopentane-acetyl}-2(S)-amino-4,4-dimethylpentanoic acid benzyl ester [Boc-Asp(pyrrolidino)-Asp(cyPn)-YMeLeu-OH dibenzoate] as a colorless foam (0.459 g, 100%).

(d) A solution of the latter compound (0.385 g, 0.5 mmol) in 30% TFA in CH$_2$Cl$_2$ was stirred at 0° for 1 h. The solvent was evaporated and the residue was dried under vacuum. The resulting TFA salt, dissolved in acetonitrile (20 mL), was coupled with (R,S)-2-(1,1-dimethylethyl)-4-oxo-4-(1-ethyl-propylamino)butanoic acid (0.146 g, 0.6 mmol, described in example 4) using BOP (0.309 g, 0.7 mmol) and NMM (0.65 mL, 6 mmol) according to the procedure described in paragraph (c) of this example. The resulting product was a mixture of two diastereoisomers. The isomers were separated by flash chromatography (SiO$_2$, eluant=EtOAc) to give a less polar isomer (0.100 g, Rf 0.71 (EtOAc)] and a more polar isomer [0.120 g, Rf 0.42 (EtOAc)]. The more polar isomer, namely the di(benzyl ester) of the title compound of this example, was subjected to hydrogenolysis (10% Pd/C in EtOH, 1 atmosphere of H$_2$, 3 h]. After the completion of the reaction, the catalyst was removed from the reaction mixture by filtration through a 45 μM membrane and the filtrate was concentrated. The residue was trituated with Et$_2$O. The resulting white solid was collected and dried under vacuum to give the title peptide of this example (51 mg, 53% yield, 92% pure as determined by HPLC).

EXAMPLE 6

Comparison of Acyclovir, the Peptide of Formula:
Et$_2$CHNHCO—CH$_2$CH[(S)-C(CH$_3$)$_3$]CO-Asp(pyrrolidino)-Asp(cyPn)-YMeLeu-OH, and the Combination of the Two Agents in Inhibiting HSV-2 Replication in Cell Culture BHK-21/C13 cells (ATCC CCL 10) are incubated for two days in 150 cm$^2$ T-flasks (1.5×10$^6$ cells/flask) with alpha-MEM medium (Gibco Canada Inc., Burlington, Ontario, Canada) supplemented with 8% (v/v) fetal bovine serum (FBS, Gibco Canada Inc.). The cells are trypsinized and then transferred to fresh media in a 24 well plate to give $2.5 \times 10^5$ cells in 750 μL of media per well. The cells are incubated at 37° C. for a period of 6 hours to allow them to adhere to the plate. Thereafter, the cells are washed once with 500 μL of alpha-MEM supplemented with 0.5% (v/v) FBS and then incubated with 750 μL of the same media (low serum) for 3 days. After this period of serum starvation, the low serum medium is removed and the cells are incubated in 500 μL of BBMT for 2 to 3 hours. [BBMT medium is described by P. Brazeau et al., Proc. Natl. Acad. Sci. USA, 79, 7909 (1982).] Thereafter, the cells are infected with HSV-2 (multiplicity of infection=0.02 PFU/cell) in 100 μL of BBMT medium. (Note: The HSV-2 used was strain HG-52, see Y. Langelier and G. Buttin, J. Gen. Virol., 57, 21 (1981); the virus was stored at −80° C.) Following 1 hour of virus adsorption at 37° C., the media is removed and the cells are washed with BBMT (3×250 μL). The cells in each well are incubated with or without (control) appropriate concentrations of the test agent-dissolved in 200 μL of BBMT medium. After 29 hours of incubation at 37° C., the infected cells are harvested by first freezing the plate at −80° C., followed by thawing. The cells in each well are scraped off the surface of the well with the help of the melting ice fragments. After complete thawing, the cell suspensions are collected and each well is rinsed with 150 μL of BBMT medium. The viral sample (suspension plus washing) is sonicated gently for 4 minutes at 4° C. Cell debris are removed by centrifugation (1000 times gravity for 10 minutes at 4° C.). The supernatant is collected and stored at −80° C. until determination of viral titer.

Viral titration was performed by a modification of the colorimetric assay method of M. Langlois et al., Journal of Biological Standardization, 14, 201 (1986).

More specifically, in a similar manner as described above, BHK-21/C13 cells are trypsinized and transferred to fresh media in a 96 well microtiter plate to give 20,000 cells in 100 μL of media per well. The cells in the prepared plate are incubated at 37° C. for 2 hours. During that time, the viral sample is thawed and sonicated gently for 15 seconds, and log dilutions of the sample are prepared (1/5 sequential: 50 μL of the sample plus 200 μL of BBMT medium, sequential dilutions being done with a multichannel pipette.

On completion of the above 2 hour incubation of the BHK-21/C13 cells, the media is replaced with alpha-MEM medium supplemented with 3% (v/v) FBS. The cells are now ready to be infected with the various sample dilutions of virus. Aliquots (50 μL) of the various dilutions are transferred into the appropriate wells of the plate. The resulting infected cells are incubated for 2 days at 37° C. Then 50 μL of a 0.15% (v/v) solution of neutral red dye in Hank's Balanced Salt Solution (pH 7.3, Gibco Canada Inc.) is added to each well. The prepared plate is incubated for 45 minutes at 37° C. Medium from each well is then aspirated and the cells are washed once with 200 μL of Hank's Balanced Salt Solution. After the wash, the dye is released from the cells by the addition of 100 μL of a 1:1 mixture of 0.1M Sorensen's citrate buffer (pH 4.2) and ethanol. [Sorensen's citrate buffer is prepared as follows: Firstly, a 0.1M disodium citrate solution is prepared by dissolving citric acid monohydrate (21 g) in 1N aqueous NaOH (200 mL) and adding sufficient filtered $H_2O$ to make 1 L. Secondly, the 0.1M disodium citrate solution (61.2 mL) is mixed with 0.1N aqueous HCl (38.8 mL) and the pH of the resulting solution is adjusted to 4.2 if necessary.] The mixture in the wells is subjected to a gentle vortex action to ensure proper mixing. The plate wells are scanned by a spectrophotometer plate reader at 540 mM to assess the number of viable cells. In this manner, the percentage of virus growth inhibition can be determined for the various concentrations of the test agent, and the concentration of the test agent causing a 50% inhibition of virus replication, i.e. the $IC_{50}$ can be calculated.

The following table is illustrative of the results obtained when acyclovir and the title peptide of formula 1 were evaluated according to the assay procedure of this example.

TABLE

| COMPOUND | RANGE OF SAMPLE CONCENTRATIONS EVALUATED | $IC_{50}$ (μM) |
|---|---|---|
| acyclovir* | 0.1 to 30 μM | 4.0 |
| peptide** | 62.5 to 1000 μM | ~1000 |
| acyclovir + 150 μM of peptide | 0.005 to 30 μM | 0.9 |
| acyclovir + 200 μM of peptide | 0.005 to 30 μM | 1.4 |
| acyclovir + 250 μM of peptide | 0.005 to 30 μM | 0.5 |
| acyclovir + 300 μM of peptide | 0.005 to 30 μM | 0.4 |

*acyclovir was obtained from Bourroughs Wellcome Inc., Kirkland, Quebec, Canada
**The title peptide of formula 1 of this example The synergism of the combination of acyclovir and the peptide of formula 1 can further be demonstrated by applying the isobole method to the above results, see J. Sühnel, Antiviral Research, 13, 23 (1990) and references therein. The positive result obtained in the application of this method is illustrated graphically in the accompanying FIG. 1.

By following the procedure of this example, synergism can be demonstrated also for other combinations of the nucleoside analogs and the peptides of formula 1. Examples of other specific peptides of formula 1 for use according to the present invention are:

$Et_2CHNH-COCH_2CH[(S)-C(CH_3)_3]CO-Asp(pyrrolidino)-Asp(cyPn)-\{(S)-NHCH[CH_2C(CH_3)_3]CH_2OH\}$ $Et_2CHNH-COCH_2CH[(S)-C(CH_3)_3]CO-Asp(pyrrolidino)-Asp(cyPn)-NHCH_2CH_2C(CH_3)_3$ $Et_2CHNH-COCH_2CH[(S)-C(CH_3)_3]CO-Asp(pyrrolidino)-Asp(CyBu)-Leu-OH$ $Me_2CHNH-COCH_2CH[(S)-C(CH_3)_3]CO-Asp(NEt_2)-Asp-(diMe)-YMeLeu-OH$ $(Cyclohexyl)CH_2NH-COCH_2CH[(S)-CH(CH_3)_2]CO-Asp-(morpholino)-Asp(cyPn)-Cpg-OH$ $Me_2CHCH_2CH_2NH-COCH_2CH[(S)-Et]CO-Asp(piperidino)-Asp(cyBu)-Cha-OH$.

The embodiments of this invention in which an exclusive property or privilege is claimed are defined as follows:

1. A pharmaceutical composition for treating herpes infections in a mammal comprising a pharmaceutically or veterinarily acceptable carrier, and the combination of an antiherpes viral nucleoside analog, or a therapeutically acceptable salt thereof, and a ribonucleotide reductase inhibiting peptide derivative of formula 1

R$^1$NHC(O)CH$_2$CHR$^2$C(O)—NR$^3$—CH[CH$_2$-C(O)—Y]C(O)—NH—CH[CR$^4$(R$^5$)COOH]—C(O)—NH—CHR$^6$—Z wherein R$^1$ is (1–10C) alkyl, (1–10C)alkyl monosubstituted with halo, hydroxy or lower alkoxy, lower cycloalkyl, (lower cycloalkyl)-(lower alkyl), phenyl(lower)alkyl or phenyl(lower)alkyl monosubstituted with halo, hydroxy or lower alkoxy;

R$^2$ is lower alkyl;

R$^3$ is hydrogen or lower alkyl;

R$^4$ is hydrogen or lower alkyl and R$^5$ is lower alkyl, or R$^4$ and R$^5$ together with the carbon atom to which they are attached form a lower cycloalkyl;

R$^6$ is lower alkyl, lower cycloalkyl or (lower cycloalkyl)-(lower alkyl);

Y is (a) NR$^7$R$^8$ wherein R$^7$ and R$^8$ each independently is lower alkyl, or R$^7$ and R$^8$ together with the nitrogen atom to which they are attached form a pyrrolidino, piperidino, morpholino, thiomorpholino, piperazino or N$^4$-methylpiperazino; or (b) (1–7C)alkyl, lower cycloalkyl or (lower cycloalkyl)methyl; and Z is hydrogen, COOH or CH$_2$OH;

or a therapeutically acceptable salt thereof, wherein the antiherpes viral nucleoside analog and the peptide, are each present in the composition in an amount effective to produce a synergistic effect in the mammal.

2. A pharmaceutical composition of claim 1 wherein the peptide is a peptide of formula 1 wherein R$^1$ is (1–10C)alkyl, (1–10C)alkyl monosubstituted with halo, hydroxy or lower alkoxy, lower cycloalkyl or (lower cycloalkyl)methyl, R$^2$ is lower alkyl, R$^3$ is hydrogen, R$^4$ and R$^5$ together with the hydrogen to which they are attached form a lower cycloalkyl, and R$^6$, Y and Z are as defined in claim 1; or a therapeutically acceptable salt thereof.

3. A pharmaceutical composition of claim 2 wherein the peptide is a peptide of formula 1 wherein R$^1$ is 1-methylethyl, 1-methylpropyl, 1-ethylpropyl, 1-methylbutyl, cyclopentyl or cyclohexyl, R$^2$ is methyl, ethyl, propyl, 1-methylethyl, butyl, 1-methylpropyl, 2-methylpropyl, 1,1-dimethylethyl or 1-methylbutyl, R$^3$, R$^4$ and R$^5$ are as defined in claim 2, R$^6$ is 1-methylethyl, 1,1-dimethylethyl, 1-methylpropyl, 2-methylpropyl, 2,2-dimethylpropyl, cyclopentyl, cyclohexyl or cyclohexylmethyl, Y is NR$^7$R$^8$ wherein R$^7$ and R$^8$ each independently is methyl, ethyl or propyl or R$^7$ and R$^8$ together with the nitrogen atom to which they are attached form a pyrrolidino, piperidino, morpholino or N$^4$-methylpiperazino, or Y is pentyl, hexyl, 4-methylpentyl, heptyl, cyclopentyl or cyclohexyl, and Z is as defined in claim 2; or a therapeutically acceptable salt thereof.

4. A pharmaceutical composition of claim 3 wherein the peptide is a peptide of formula 1 wherein R$^1$ is 1-methylethyl or 1-ethylpropyl, R$^2$ is 1-methylethyl or 1,1-dimethylethyl, R$^3$ is hydrogen, R$^4$ and R$^5$ together with the carbon atom to which they are attached form a cyclobutyl or cyclopentyl, R$^6$ is 2,2-dimethylpropyl, Y is N,N-dimethylamino, N,N-diethylamino, pyrrolidino, morpholino or N$^4$-methylpiperazino, hexyl, heptyl or cyclopentyl, and Z is as defined in claim 3; or a therapeutically acceptable salt thereof.

5. A pharmaceutical composition of claim 4 wherein the peptide is selected from the group consisting of:

Et$_2$CHNH-COCH$_2$CH[(S)-C(CH$_3$)$_3$]CO-Asp(pyrrolidino)-Asp(cyPn)-YMeLeu-OH

Et$_2$CHNH-COCH$_2$CH[(S)-C(CH$_3$)$_3$]CO-Asp(pyrrolidino)-Asp(cyPn)-{(S)-NHCH[CH$_2$C(CH$_3$)$_3$]CH$_2$OH} and Et$_2$CHNH-COCH$_2$CH[(S)-C(CH$_3$)$_3$]CO-Asp(pyrrolidino)-Asp(cyPn)-NHCH$_2$CH$_2$C(CH$_3$)$_3$;

or a therapeutically acceptable salt thereof.

6. A pharmaceutical composition of claim 1 wherein the nucleoside analog is a compound of formula 2

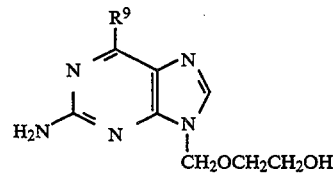

wherein R$^9$ is hydrogen, hydroxy or amino, or a therapeutically acceptable salt thereof.

7. A pharmaceutical composition of claim 1 wherein the antiherpes viral nucleoside analog is selected from the group of vidarabine, idoxuridine, trifluridine, ganciclovir, edoxudine, brovavir, fiacitabine, penciclovir, famciclovir and rociclovir.

8. A pharmaceutical composition of claim 1 wherein the amount of the nucleoside analog, or a therapeutically acceptable salt thereof, is 0.01–1.0% by weight of the composition, and the amount of the peptide of formula 1, or a therapeutically acceptable salt thereof, is 0.5–20% by weight of the composition.

9. A pharmaceutical composition of claim 6 comprising 0.05–1.0% by weight of the compound of formula 2 wherein R$^9$ is hydroxy, and 1–10% by weight of the peptide of formula 1 wherein R$^2$ is (S)-1,1-dimethylethyl, R$^4$ and R$^5$ together with the carbon atom to which they are attached form a cyclobutyl or cyclopentyl and R$^6$ is 2,2-dimethylpropyl.

10. A cosmetic composition comprising an antiherpes viral amount of a combination of an antiherpes viral nucleoside analog of formula 2

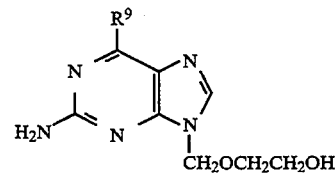

in which R$^9$ is hydrogen, hydroxy or amino, or a therapeutically acceptable salt thereof, and a ribonucleotide reductase inhibiting peptide of formula 1

R$^1$NHC(O)CH$_2$CHR$^2$C(O)—NR$^3$—CH[CH$_2$-C(O)—Y]C(O)—NH—CH[CR$^4$(R$^5$COOH]—C(O)—NH—CHR$^6$—Z wherein R$^1$–R$^6$, Y and Z are as defined in claim 1, or a therapeutically acceptable salt thereof, and a physiologically acceptable carrier, wherein the antiherpes viral nucleoside analog and the peptide, are each present in the composition in an amount effective to produce a synergistic effect.

11. A method of treating herpes viral infections in a mammal in need of such treatment, comprising administering thereto an effective amount of a combination of an antiherpes viral nucleoside analog, or a therapeutically acceptable salt thereof, and a ribonucleotide reductase inhibiting peptide of formula 1

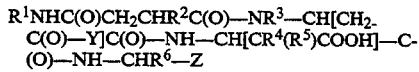

wherein $R^1$-$R^6$, Y and Z are as defined in claim 1, or a therapeutically acceptable salt thereof, wherein the antiherpes viral nucleoside analog and the peptide, are each present in the combination in an amount effective to produce a synergistic effect in the mammal.

12. A method of claim 11 wherein the nucleoside analog and the peptide of formula 1 are administered sequentially or simultaneously.

13. A method of claim 11 wherein the combination is administered topically.

14. A method of claim 11 wherein the antiviral nucleoside analog is selected from the group of acyclovir, 6-deoxyacylovir, 2,6-diamino-9-[(2-hydroxyethoxy)methyl]purine, vidarabine, idoxuridine, trifluridine, gangciclovir, edoxudine, brovavir, fiacitabine, penciclovir, famciclovir and rociclovir.

15. A method of treating herpes simplex virus type 1 or type 2, infections in a mammal in need of such treatment, comprising administering thereto an effective amount of the pharmaceutical composition of claim 6 wherein the peptide of formula 1 of the composition is selected from the group consisting of:

Et₂CHNH-COCH₂CH[(S)-C(CH₃)₃]CO-Asp(pyrrolidino)-Asp(cyPn)-YMeLeu-OH,

Et₂DHNH-COCH₂CH[(S)-C(CH₃)₃]-Asp(pyrrolidino)-Asp(cyPn)-{(S)-NHCH[CH₂C(CH₃]CH₂OH}, and Et₂CHNH-COCH₂CH[(S)-C(CH₃)₃]CO-Asp(pyrrolidino)-Asp(cyPn)-NHCH₂CH₂C(CH₃)₃;

or a therapeutically acceptable salt thereof.

16. A pharmaceutical composition for treating herpes infections in a mammal comprising a pharmaceutically or veterinarily acceptable carrier, and an effective amount of the combination of an antiherpes vital nucleoside analog of the formula

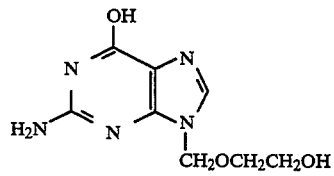

or a therapeutically acceptable salt thereof, and a ribonucleotide reductase inhibiting peptide of the formula

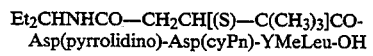

or a therapeutically acceptable salt thereof, wherein the antiherpes viral nucleoside analog and the peptide, are each present in the composition in an amount effective to produce a synergistic effect in the mammal.

* * * * *